(12) United States Patent
Tobin et al.

(10) Patent No.: US 9,849,279 B2
(45) Date of Patent: Dec. 26, 2017

(54) LEAD DELIVERY DEVICE AND METHOD

(75) Inventors: Lindsey Marie Tobin, Minneapolis, MN (US); Andrea Jean Asleson, Maple Grove, MN (US); Steven Lawrence Waldhauser, Circle Pines, MN (US); Scott William Hayden, Maple Grove, MN (US); Kendra Yasger, Big Lake, MN (US); Ronald Alan Drake, Saint Louis Park, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 829 days.

(21) Appl. No.: 12/183,105

(22) Filed: Jul. 31, 2008

(65) Prior Publication Data

US 2009/0326630 A1 Dec. 31, 2009

Related U.S. Application Data

(60) Provisional application No. 61/076,183, filed on Jun. 27, 2008.

(51) Int. Cl.
*A61N 1/05* (2006.01)

(52) U.S. Cl.
CPC ...... *A61N 1/056* (2013.01); *A61N 2001/0585* (2013.01)

(58) Field of Classification Search
USPC ........... 607/122, 125, 127; 600/381, 585; 604/103.06
See application file for complete search history.

(56) References Cited

U.S. PATENT DOCUMENTS

| 4,215,703 A | 8/1980 | Wilson |
| 4,497,326 A | 2/1985 | Curry et al. |

(Continued)

FOREIGN PATENT DOCUMENTS

| EP | 0861676 | 9/1998 |
| EP | 2197540 A1 | 6/2010 |

(Continued)

OTHER PUBLICATIONS (PCT/US2009/048542) PCT Notification of Transmittal of the International Search Report and the Written Opinion of the International Searching Authority, 13 pages.

(Continued)

*Primary Examiner* — Erica Lee
(74) *Attorney, Agent, or Firm* — Mueting, Raasch & Gebhardt, P.A.

(57) ABSTRACT

A medical apparatus includes an electrically conductive lead for a medical device, the lead having an internal bore terminating at a distal lead opening, and a lead delivery device for delivering the distal end of the lead to a blood vessel during implantation of the lead. The lead delivery device includes a removably anchorable guidewire, and a fixator attached to a distal portion of the guidewire for anchoring the guidewire. The fixator is movable between a compact configuration and an expanded configuration. The fixator is capable of passing through the distal lead opening of the lead in the compact configuration. The fixator is capable of exerting a holding force in the range of about 0.89 to 4.45 N in the lumen of the blood vessel in the expanded configuration.

9 Claims, 8 Drawing Sheets

(56) References Cited

U.S. PATENT DOCUMENTS

| | | |
|---|---|---|
| 4,619,246 A | 10/1986 | Molgaard-Nielsen et al. |
| 5,125,904 A | 6/1992 | Lee |
| 5,147,377 A | 9/1992 | Sahota |
| 5,167,239 A * | 12/1992 | Cohen et al. ............... 600/585 |
| 5,181,911 A | 1/1993 | Shturman |
| 5,224,491 A | 7/1993 | Mehra |
| 5,265,622 A | 11/1993 | Barbere |
| 5,279,299 A | 1/1994 | Imran |
| 5,295,958 A | 3/1994 | Shturman |
| 5,312,355 A | 5/1994 | Lee |
| 5,364,340 A | 11/1994 | Coll |
| 5,409,463 A | 4/1995 | Thomas et al. |
| 5,437,083 A | 8/1995 | Williams et al. |
| 5,449,372 A | 9/1995 | Schmaltz et al. |
| 5,456,667 A | 10/1995 | Ham et al. |
| 5,456,705 A | 10/1995 | Morris |
| 5,474,563 A | 12/1995 | Myler et al. |
| 5,549,553 A | 8/1996 | Ressemann et al. |
| 5,653,684 A | 8/1997 | Laptewicz et al. |
| 5,693,014 A | 12/1997 | Abele et al. |
| 5,735,869 A | 4/1998 | Fernandez-Aceytuno |
| 5,741,320 A | 4/1998 | Thornton et al. |
| 5,803,928 A * | 9/1998 | Tockman et al. ............ 607/122 |
| 5,833,707 A | 11/1998 | McIntyre et al. |
| 5,902,331 A | 5/1999 | Bonner et al. |
| 5,954,761 A | 9/1999 | Machek et al. |
| 5,957,903 A | 9/1999 | Mirzaee et al. |
| 6,010,498 A | 1/2000 | Guglielmi |
| 6,014,589 A | 1/2000 | Farley et al. |
| 6,033,413 A | 3/2000 | Mikus et al. |
| 6,122,552 A | 9/2000 | Tockman et al. |
| 6,152,946 A | 11/2000 | Broome et al. |
| 6,161,029 A | 12/2000 | Spreigl et al. |
| 6,196,230 B1 | 3/2001 | Hall et al. |
| 6,322,559 B1 | 11/2001 | Daulton et al. |
| 6,331,190 B1 * | 12/2001 | Shokoohi ............... A61F 2/07 623/1.16 |
| 6,415,187 B1 | 7/2002 | Kuzma et al. |
| 6,416,510 B1 | 7/2002 | Altman et al. |
| 6,428,489 B1 | 8/2002 | Jacobsen et al. |
| 6,595,989 B1 | 7/2003 | Schaer |
| 6,602,271 B2 | 8/2003 | Adams et al. |
| 6,662,045 B2 | 12/2003 | Zheng et al. |
| 6,697,677 B2 | 2/2004 | Dahl et al. |
| 6,928,313 B2 | 8/2005 | Peterson |
| 6,931,286 B2 | 8/2005 | Sigg et al. |
| 6,970,742 B2 | 11/2005 | Mann et al. |
| 7,037,290 B2 | 5/2006 | Gardeski et al. |
| 7,092,765 B2 | 8/2006 | Geske et al. |
| 7,107,105 B2 | 9/2006 | Bjorklund et al. |
| 7,171,275 B2 | 1/2007 | Hata et al. |
| 7,344,557 B2 * | 3/2008 | Yadin ..................... 623/1.11 |
| 7,765,014 B2 | 7/2010 | Eversull et al. |
| 7,976,551 B1 | 7/2011 | Gutfinger et al. |
| 8,229,572 B2 | 7/2012 | Drake et al. |
| 8,394,079 B2 | 3/2013 | Drake et al. |
| 8,920,432 B2 | 12/2014 | Drake et al. |
| 2002/0077686 A1 | 6/2002 | Westlund et al. |
| 2002/0147487 A1 | 10/2002 | Sundquist et al. |
| 2002/0173835 A1 | 11/2002 | Bourang et al. |
| 2003/0028234 A1 | 2/2003 | Miller et al. |
| 2003/0088194 A1 * | 5/2003 | Bonnette et al. ............. 600/585 |
| 2003/0120208 A1 | 6/2003 | Houser et al. |
| 2003/0204231 A1 | 10/2003 | Hine et al. |
| 2003/0225434 A1 | 12/2003 | Glantz et al. |
| 2003/0229386 A1 | 12/2003 | Rosenman et al. |
| 2004/0059348 A1 | 3/2004 | Geske et al. |
| 2004/0116878 A1 | 6/2004 | Byrd et al. |
| 2004/0162599 A1 | 8/2004 | Kurth |
| 2004/0215298 A1 | 10/2004 | Richardson et al. |
| 2004/0242990 A1 | 12/2004 | Brister et al. |
| 2005/0089655 A1 | 4/2005 | Lim |
| 2005/0113862 A1 | 5/2005 | Besselink et al. |
| 2005/0215990 A1 | 9/2005 | Govari |
| 2006/0106445 A1 * | 5/2006 | Woollett ............ A61N 1/056 607/122 |
| 2006/0210605 A1 | 9/2006 | Chang et al. |
| 2006/0241737 A1 | 10/2006 | Tockman et al. |
| 2006/0259063 A1 | 11/2006 | Bates et al. |
| 2006/0292912 A1 | 12/2006 | Bjorklund et al. |
| 2007/0016240 A1 | 1/2007 | Warnack et al. |
| 2007/0043413 A1 | 2/2007 | Eversull et al. |
| 2007/0079511 A1 | 4/2007 | Osypka |
| 2007/0100409 A1 | 5/2007 | Worley et al. |
| 2007/0100410 A1 * | 5/2007 | Lamson et al. ............. 607/119 |
| 2007/0250144 A1 * | 10/2007 | Falk et al. .................... 607/122 |
| 2008/0021336 A1 | 1/2008 | Dobak, III |
| 2008/0065013 A1 | 3/2008 | Goodin |
| 2008/0103537 A1 | 5/2008 | Sigg et al. |
| 2008/0103575 A1 | 5/2008 | Gerber |
| 2008/0183255 A1 * | 7/2008 | Bly et al. ..................... 607/116 |
| 2008/0195226 A1 | 8/2008 | Williams et al. |
| 2008/0300664 A1 | 12/2008 | Hine et al. |
| 2009/0143768 A1 | 6/2009 | Parodi et al. |
| 2009/0326551 A1 | 12/2009 | Drake et al. |
| 2009/0326629 A1 | 12/2009 | Drake et al. |
| 2009/0326630 A1 | 12/2009 | Tobin et al. |
| 2010/0016863 A1 | 1/2010 | Drake et al. |
| 2010/0016864 A1 | 1/2010 | Drake et al. |
| 2010/0036473 A1 | 2/2010 | Roth |
| 2015/0174394 A1 | 6/2015 | Drake et al. |

FOREIGN PATENT DOCUMENTS

| | | |
|---|---|---|
| EP | 2344236 A2 | 7/2011 |
| WO | WO 2004/026371 A2 | 4/2004 |
| WO | WO 2005/053784 A2 | 6/2005 |
| WO | WO 2008/101078 A2 | 8/2008 |
| WO | WO 2009/158444 A1 | 12/2009 |
| WO | WO 2010/014413 A2 | 2/2010 |
| WO | WO 2010/014413 A3 | 4/2010 |
| WO | WO 2010/138648 A1 | 12/2010 |

OTHER PUBLICATIONS

International Search Report and Written Opinion for PCT patent application PCT/US2009/050783, dated Mar. 3, 2010; 15 pages.
International Search Report and Written Opinion for PCT patent application PCT/US2010/036280, dated Aug. 27, 2010; 9 pages.

* cited by examiner

LEAD DELIVERY DEVICE AND METHOD

CROSS-REFERENCE TO RELATED APPLICATIONS

This application claims the benefit of U.S. Provisional Application No. 61/076,183, filed on Jun. 27, 2008.

This application is related to U.S. patent application Ser. No. 11/468,910 filed on Aug. 31, 2006, which is a division of U.S. patent application Ser. No. 10/254,196, filed on Sep. 24, 2002, now U.S. Pat. No. 7,107,105.

The disclosures of the above applications are incorporated herein by reference.

INTRODUCTION

Various cardiac devices providing electrical stimulation, rhythm management, or resynchronization therapy to the heart include electrically conductive leads in contact with excitable heart or other body tissue.

The present teachings provide a device and method for delivering an electrically conductive lead to a target site for a use with a cardiac or other medical device.

SUMMARY

The present teachings provide a medical apparatus that includes an electrically conductive lead for a medical device, the lead having an internal bore terminating at a distal lead opening, and a lead delivery device for delivering the distal end of the lead to a blood vessel during implantation of the lead. The lead delivery device includes a removably anchorable guidewire, and a fixator attached to a distal portion of the guidewire for anchoring the guidewire. The fixator is movable between a compact configuration and an expanded configuration. The fixator is capable of passing through the distal lead opening of the lead in the compact configuration. The fixator is capable of exerting a holding force in the range of about 0.89 to 4.45 N in the lumen of the blood vessel in the expanded configuration.

The present teachings also provide a medical method that includes inserting a distal end of cannulated catheter through cardiac tissue into a main cardiac vessel, attaching an expandable fixator to a distal portion of a guidewire, inserting the guidewire through the catheter, advancing the guidewire past the distal end of the catheter and into a target site in a lumen of a branching vessel, expanding the fixator into the target site, removably anchoring the fixator into the lumen with a holding force in the range of about 0.89 to 4.45 N, and removing the catheter. The method further includes advancing an electrically conductive lead of a medical device over the guidewire to the target site without moving the guidewire while tensioning the guidewire, and delivering the distal portion of the lead at the target site.

In another aspect, the present teachings provide a medical apparatus that includes a medical device for providing cardiac therapy, or cardiac sensing, or a combination thereof, an electrically conductive lead having proximal and distal ends, the proximal end couplable to the medical device, the lead having an internal bore terminating at a distal opening at the distal end, and a lead delivery device for delivering the distal end of the lead to a blood vessel during implantation of the lead. The lead delivery device includes a removably anchorable guidewire, and a fixator attached to a distal portion of the guidewire, the fixator movable between a compact configuration and an expanded configuration. The fixator has a compact width less or equal to about 0.483 mm and is capable of passing through the distal lead opening of the lead in the compact configuration. The fixator has an expanded width up to about 5 mm, and is capable of exerting a holding force in the range of about 0.89 to 4.45 N in the lumen of the blood vessel in the expanded configuration.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. The present teachings are applicable to any devices that require implantation of electrically conductive leads, including pacemakers, defibrillators or other medical devices providing rhythm management, resynchronization therapy or other cardiac therapy.

During left heart (LH) lead delivery methods for implanting cardiac therapy devices, cannulated catheters can be used to provide support and stiffness and allow trackability of the lead into the coronary sinus and more acute branching vessels. For example, in Cardiac Resynchronization Therapy (CRT), a special third lead that is implanted via the Coronary Sinus (CS) and positioned in a sub-selected cardiac vein to sense and/or pace the left ventricle in combination with atrial-synchronized, biventricular pacing using standard pacing technology. Following a sensed atrial contraction or atrial-paced event, both ventricles are stimulated to synchronize their contraction. The resulting ventricular resynchronization reduces mitral regurgitation and optimizes left ventricular filling, thereby improving cardiac function.

Guidewires can be used inside the Coronary Sinus and Great Cardiac Vein to gain access to acute side branches. A guidewire is placed into the targeted vessel and the lead is placed over the guidewire and through the catheter. Under existing methods, during lead delivery, a compressive force is maintained by a forward pressure on both the guidewire and lead to allow the lead to travel distally in the branching veins at the target site. The lead itself is designed to provide stiffness and steerability characteristics for the purpose of placement into the vessels. After the LH lead has reached its desired location, the delivery catheters used during the procedure must be removed by slitting because the proximal end of the lead is larger in diameter that the bore of the catheter and the catheter cannot be removed over the lead. The slitting procedure requires a very specific skill set, provides multiple avenues for user error and places constraints on catheter design, construction and use.

In contrast to the existing method described above, the present teachings provide a lead delivery device method that does not require slitting the catheter. The lead delivery device includes a guidewire that can be temporarily anchored in a sub-selected acute coronary vein branch during lead delivery. Fixation can be provided by a fixator that expands from a compact configuration of very low profile fitting inside a lead to an expanded configuration having a dimension large enough to allow sufficient tension to be placed on the guidewire to enable lead delivery over the guidewire in a zip-line or rope-climbing manner, as described below. The guidewire with the fixator in the compact configuration can be guided through the catheter to the target site. The catheter can then be removed before the lead is advanced over the guidewire. After the lead is implanted, the fixator is returned to the compact configuration and removed together with the guidewire through the implanted lead without slitting.

Figure 1:
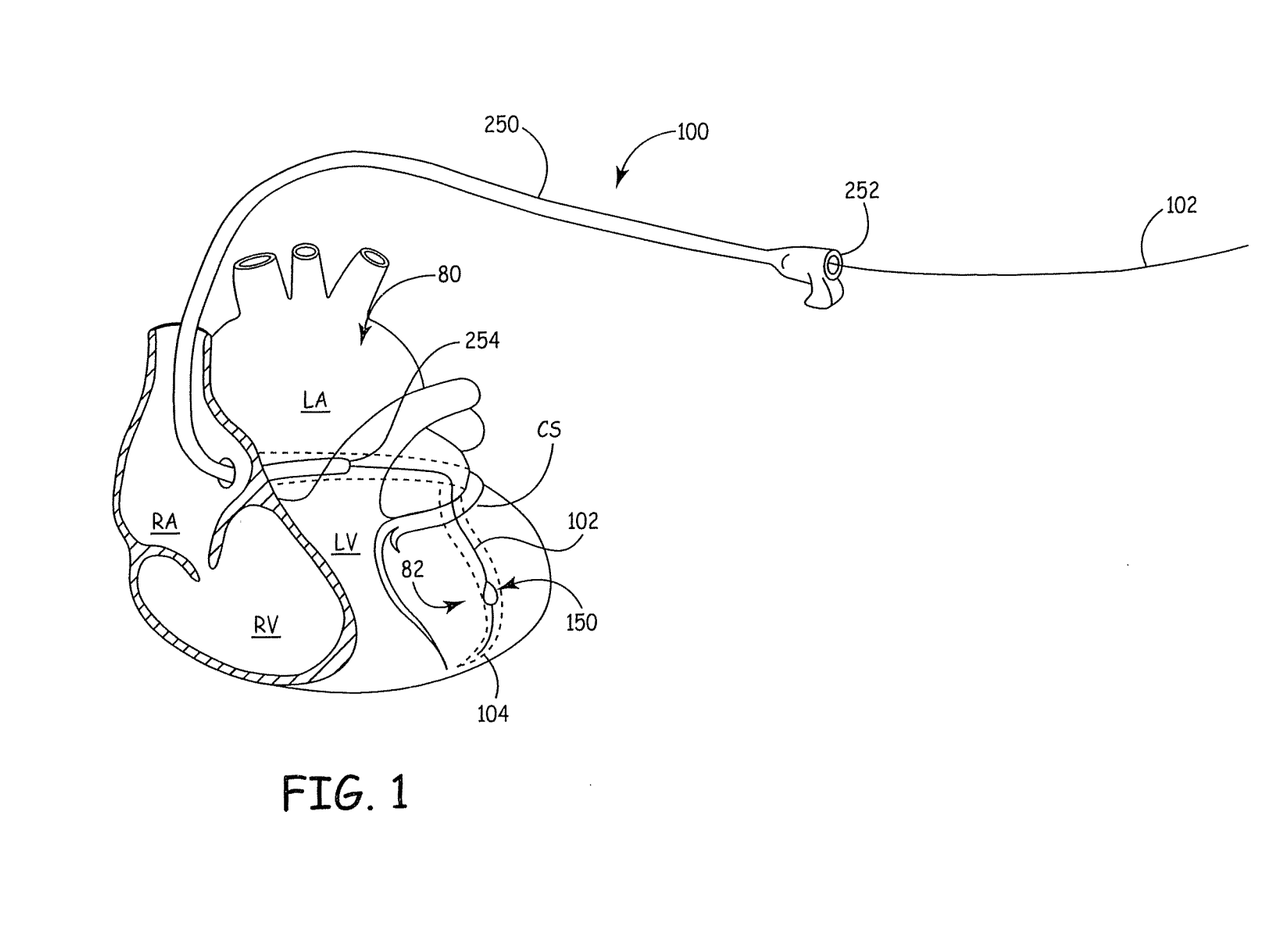
FIG. 1 is an environmental view of a lead delivery device according to the present teachings shown in a first aspect.
Figures 1A, 1B:
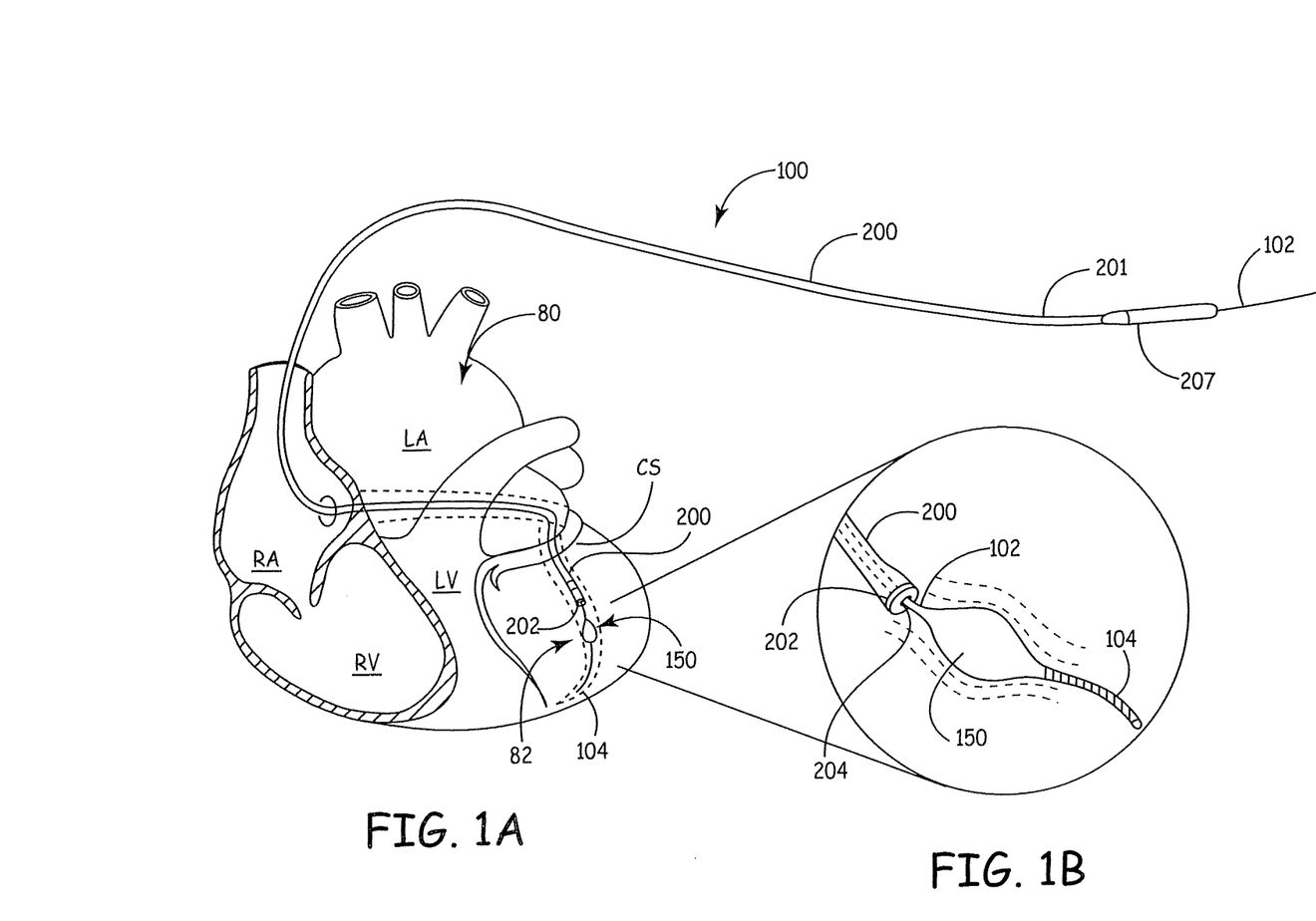
FIG. 1A is an environmental view of the lead delivery device of FIG. 1, shown in a second aspect.
FIG. 1B is an enlarged detail of the lead delivery device of FIG. 1B.
Figure 2:
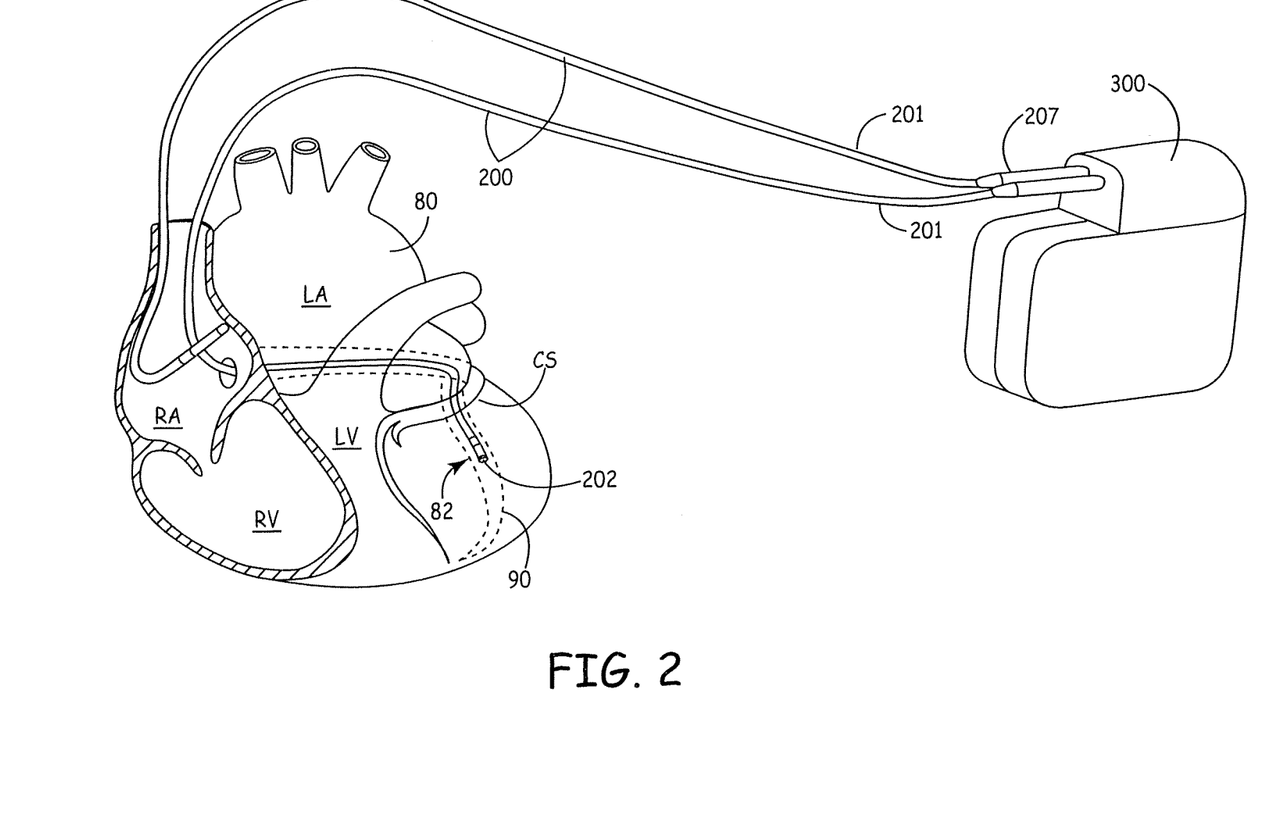
FIG. 2 is a perspective environmental view of the medical device with the lead implanted after the lead delivery device of FIG. 1B is removed.

An exemplary lead delivery device 100 according to the present teachings is illustrated during lead delivery of an electrically conductive lead 200 in FIGS. 1, 1A and 1B. An implanted lead 200 is shown in FIG. 2, after the lead delivery device 100 is removed. The lead 200 can be cannulated having an internal bore or lumen 204, a proximal portion 201, and a distal portion 202. The proximal portion 201 can be coupled with a connector pin 207 to a connector block of a cardiac or other medical device 300, with which the lead 200 is in electrical communication. A catheter 250 having a proximal end 252 and a distal end 254 can be used to insert the lead delivery device initially through heart tissue 80, as shown in FIG. 1.

The lead delivery device 100 can include a guidewire 102 entering a proximal end 252 of the catheter 250 and exiting through a distal end 254 of the catheter 250 as shown in FIG. 1. The guidewire 102 can be solid or cannulated with a bore 103, as shown in FIG. 12. The guidewire 102 can include a distal portion 104 terminating in a tip 106. The distal portion 104 can be flexible for ease in guiding the guidewire 102 through tortuous blood vessels to a target site 82, such as a branching vein branching off the coronary sinus or other main blood vessel. The lead delivery device 100 can include a fixator 150 coupled to the guidewire 102. The fixator 150 can assume an expanded or deployed configuration for anchoring the guidewire 102 near a target site 82 during lead delivery and implantation, as shown in FIGS. 3, and 5-11, illustrating various fixator aspects. Referring to FIG. 1A, the catheter 250 can be removed by retracting the catheter 250 from heart tissue 80 after the lead delivery device is anchored at the target site 82. No slitting of the catheter 250 is required for removal of the catheter 250. After the catheter 250 is removed, the lead 200 can be guided over the guidewire 102 to the target site 82, as discussed further below.

Figure 3:
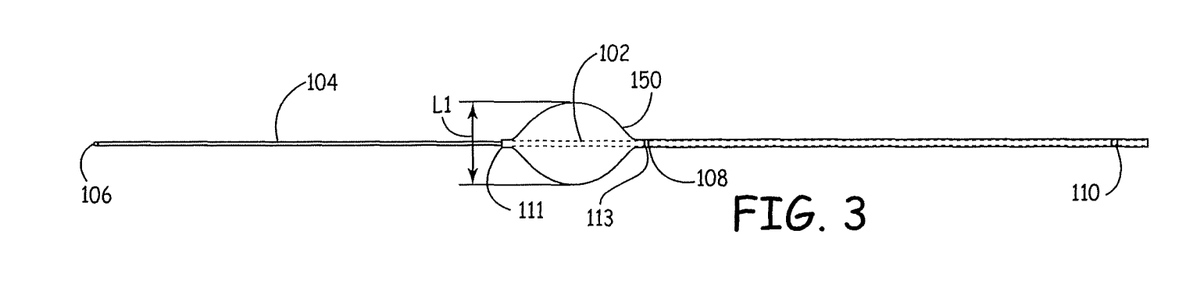
FIG. 3 is a plan view of a lead delivery device having a fixator according to the present teachings, the lead delivery device shown with the fixator in an expanded configuration.
Figure 4:
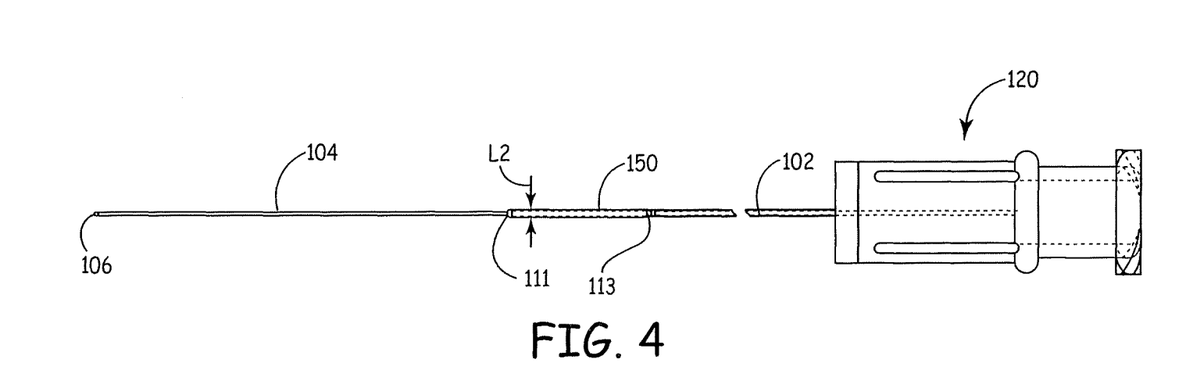
FIG. 4 is a plan view of a lead delivery device having a fixator according to the present teachings, the lead delivery device shown with the fixator in a compact configuration.

The fixator 150 can be returned to a compact or undeployed configuration, such as the configuration illustrated in FIG. 4, for retracting and removing the guidewire 102 after lead delivery and implantation. The maximum dimension, diameter or width of the fixator 150 in the expanded configuration is denoted as L1 and in the contracted configuration as L2, as illustrated in FIGS. 3 and 4 for a fixator in the form of a balloon.

FIGS. 5-11 illustrate various fixators 150 in their expanded configuration showing the maximum dimension L1 for each fixator 150. The dimension L1 is selected to achieve a fixation force within a blood vessel of an amount that allows the guidewire 102 to be pulled in tension without being dislodged from the blood vessel while the lead is pushed over the guidewire 102, as discussed below. The fixation force F can be equal to or greater than about 2.24 N, or about 0.5 lbf for achieving sufficient fixation within the blood vessel wall. The fixation force F can generally be in the range of about 0.89 to 4.45 N (or 0.2 to 1.0 lbs), depending on various factors, including the geometry of the branching vessel. The deployed width or dimension L1 corresponding to this fixation force F can be 5 mm, while the undeployed width or dimension L2 can be maintained to equal to or less than about 0.019 inches, or about 0.483 mm, to allow easy passage through commercially available leads, such as those used with medical devices available from Medtronic, Inc., of Minneapolis, Minn.

Figure 13:
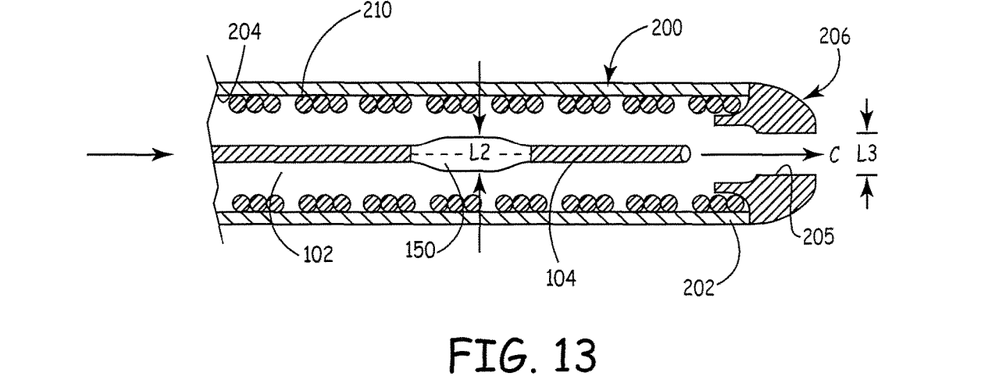
FIG. 13 is a sectional view of a lead delivery device according to the present teachings with a fixator in a compact configuration inside a lead.
Figure 14:
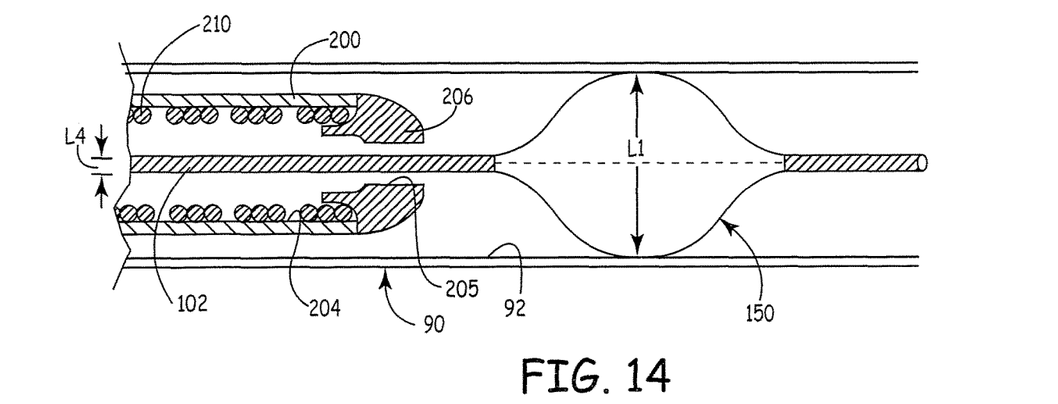
FIG. 14 is the lead delivery device of FIG. 13, shown with the fixator in an expanded configuration outside the lead.
Figure 15:
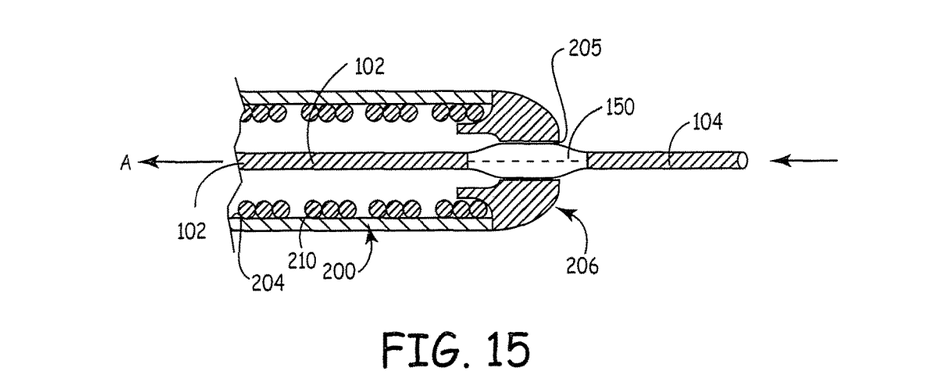
FIG. 15 is the lead delivery device of FIG. 13, shown with the fixator partially retracted inside the lead.

Referring to FIGS. 13-15, the distal portion 202 of an electrical lead 200 is illustrated in connection with a guidewire 102 having a width L4 and a fixator 150 having an undeployed width L2. The lead 200 is conductive and can deliver therapy in the form of electric energy at the target site 82. In one aspect, the lead 200 can also sense and relay information about electrical activity from the heart tissue 80 or target site 82 back to the medical device 300. The lead 200 can have an internal bore or lumen 204, an internal coil or other conductive element 210 and a tip portion 206 that can be an electrode tip with or without a seal. The tip portion 206 can define a distal opening 205 with width L3. In one aspect, the tip portion 206 can include a seal with flexible flaps, not shown. The guidewire width L4 can be about 0.346 mm (or about 0.014 inches) for providing steerability, stiffness and sufficient support for lead delivery over the guidewire 102.

Figure 16:
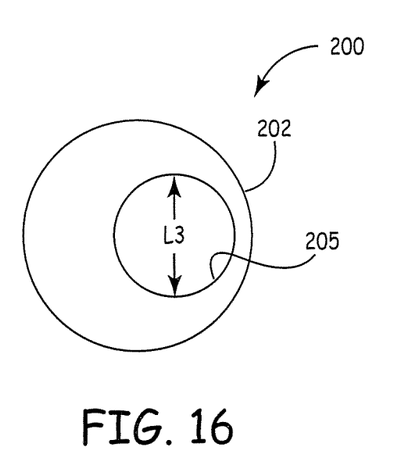
FIG. 16 is an end view of a distal end of an electrical lead with an offset distal opening.

The compact width L2 of the fixator 150 can be equal to or less than the width L3 of the distal opening 205, such that the fixator 150 can be pushed through the distal opening 205 in the direction C, as shown in FIG. 13. In one aspect the distal opening 205 can be offset relative to a central longitudinal axis of the lead 200, as shown in FIG. 16. The fixator 150 can be deployed to the expanded configuration within the blood vessel 90 such that the expanded width L1 of the fixator 150 can press against the internal lumen 92 of the blood vessel 90 with a holding force F, as discussed above, for temporarily anchoring the guidewire 102 into the blood vessel 90, as shown in FIG. 14.

Figure 5:
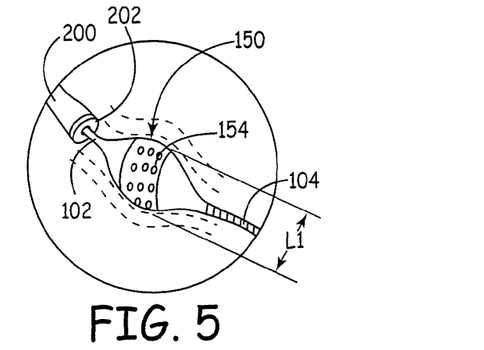
FIGS. 5-11 illustrate various fixators for a lead delivery device according to the present teachings.
Figure 7:
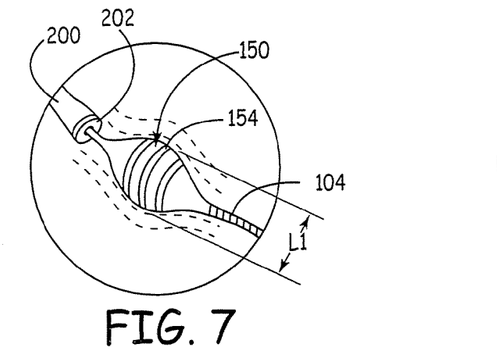

Various fixators 150 can be used to temporarily and removably anchor the guidewire 102 in the lumen 92 of a blood vessel 90. Referring to FIGS. 3 and 4, the fixator 150 can be a balloon having first and second ends 111, 113 attached to the guidewire 102. The balloon can be inflated, for example, with a gas or a fluid, including a gel or other liquid provided by a syringe through a valve 110 at a proximal end of the guidewire 102. In another aspect, a luer lock inflation port 120 can be coupled to the guidewire 102 for deploying the balloon. The balloon can be made from a polyblend material which is heated and stretched, placed around the guidewire 102 and bonded at first and second ends 111, 113 of the balloon onto the guidewire 102 with small amounts of cyanoacrylate adhesive, for example. A radio-opaque marker 108 in the form of a band can be placed adjacent the second (proximal) end 113 of the balloon for visualization during guided navigation. The radio-opaque marker 108 can also be in the form of a radio-opaque balloon coating or radio-opaque fluid filling the balloon. In another aspect, the balloon-type fixator 150 can include an etched fixation surface with etched surface fixation formations 154 in the form of bumps, rings, etc, as illustrated in FIGS. 5 and 7. In another aspect, the fixator 150 can be a balloon with spiral or helical or otherwise curved configuration for maintaining a percentage of blood flow through the blood vessel 90 and aiding fixation in tortuous anatomy.

Figure 9:
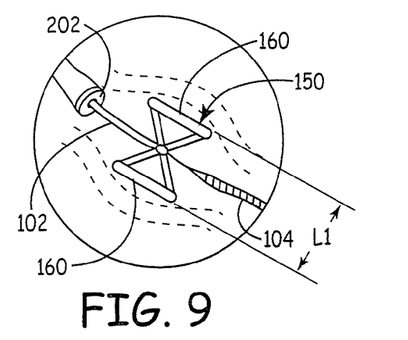
Figure 10:
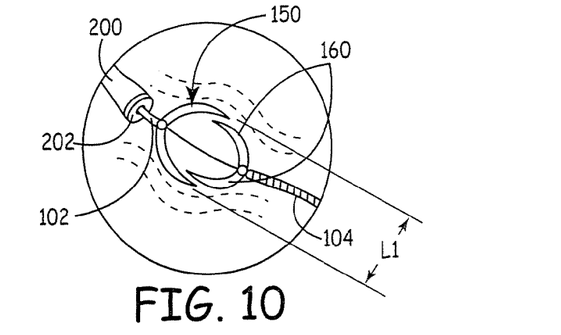
Figures 11, 11A:
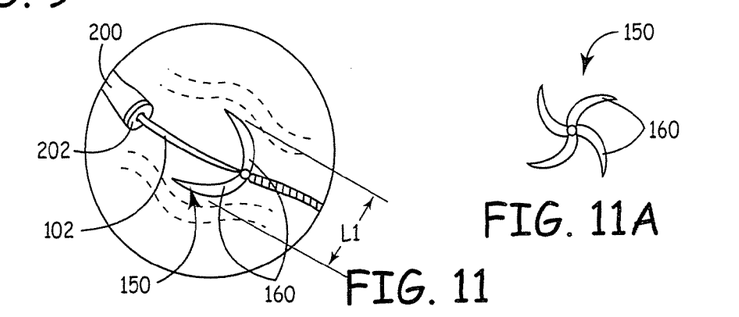
FIG. 11A is a top view of the fixator of FIG. 11.
Figure 12:
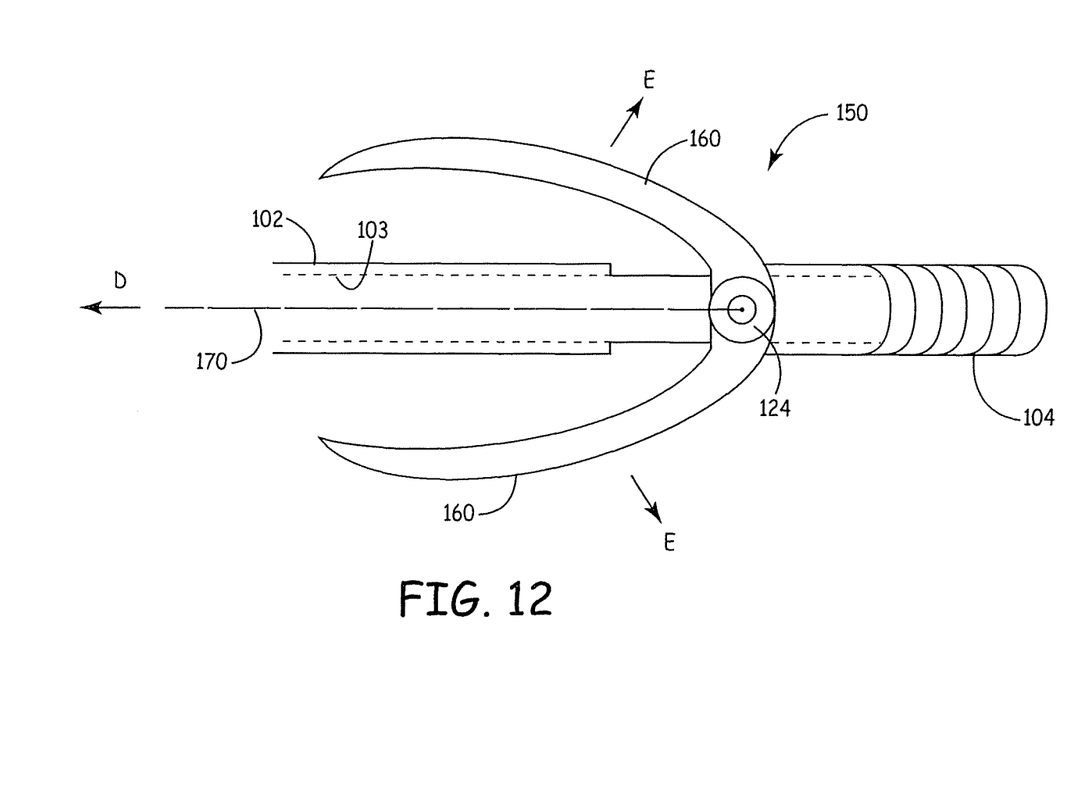
FIG. 12 is a side view of the fixator of FIG. 11, illustrating a deployment mechanism.

Referring to FIGS. 9-12, the fixator 150 can also be in the form of a mechanical anchor with deployable straight wings 160, as shown in FIG. 9, or curved wings 160, as shown in FIG. 10, or a pinwheel-type fixator 150, as shown in FIGS. 11 and 11A. The mechanical anchor 150 can be deployed with a longitudinal actuator 170 in the form of a wire or string or other elongated member passing through the bore 103 of a cannulated guidewire 102. Referring to FIG. 12, for example, the anchor wings 160 can pivot about a pivot pin 124 connected to the actuator 170 and can be deployed to the expanded position in the direction of arrows E by pulling the actuator 170 in the direction of arrow D. In other aspects, the fixator 150 can be in the form of a superelastic wire, such as nitinol, and can be pre-shaped to expand to an anchorable configuration within the blood vessel 90.

Figure 6:
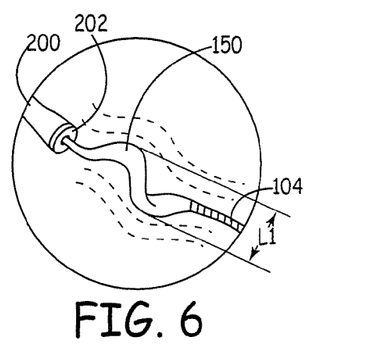
Figure 8:
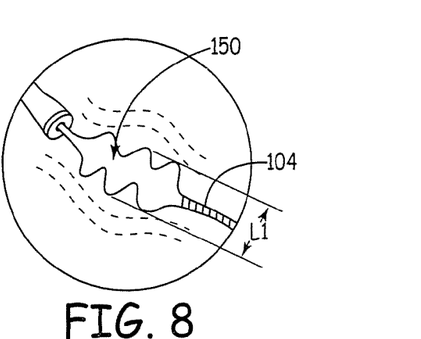

In another aspect, fixators 150 including polymer lobes or superelastic or memory-shape wire can be used. Further, the dimensions of the fixator 150, including the expanded width L1 and the compact width L2 can be selected to match the range of most common vessel sizes. The expanded shape of the fixator 150 can be selected to increase the contact area with the blood vessel and or provide multiple contact surfaces for increasing holding force and stability, as shown in FIGS. 6, 8, and 10, for example. The expanded shape can have a symmetric profile, as shown in FIG. 9, for example, or a non-symmetric profile, as shown in FIG. 6, for example. In other aspects, the expanded shape can have an asymmetric profile for anchoring unidirectionally rather than bi-directionally.

As discussed above, deployment of the fixator 150 and anchoring can occur after the cannulation of the coronary sinus CS with the catheter 250 and after sub-selection of a side branch with the guidewire 102. Further, fixation of the guidewire 102 by the expandable fixator 150 can be maintained during lead delivery and terminated after the lead 200 is delivered to the target vessel at the target site 82. At the discretion of the operating physician, fixation and release can occur multiple times during the medical procedure. Damage to the lead 200 during fixation can be avoided because fixator expansion and fixation occurs outside the lead 200.

It should be appreciated, that according to the present teachings the lead delivery device 100 with either a balloon or mechanical fixator 150 is configured and designed to function as a wedge or anchoring device for temporarily anchoring the guidewire 102 during the implantation of the electrical lead 200.

Referring to FIGS. 1-2, and 13-15, the cannulated catheter 250 can be inserted through heart tissue 80 into a coronary sinus CS, cardiac great vein or other main vessel stopping short of a target site 82 that is located in a sub-selected acute branching vessel 90. The guidewire 102 with the fixator 150 in the undeployed compact configuration can be inserted through the catheter 250, advanced past the distal end 254 of the catheter 250 through a main vessel to the target site 82 in the branching vessel 90, as shown in FIG. 1. The fixator 150 can then be deployed and become anchored in the lumen 92 of the branching vessel 90 with a holding force F, as discussed above. The catheter 250 can then be retracted and completely removed with no slitting procedure. The lead 200 can be guided over the anchored guidewire 102 until the distal portion 202 of the lead 200 reaches the target site 82, as shown in FIG. 1B. The lead 200 can be advanced by keeping the guidewire 102 in tension while pushing the lead 200 in the direction of the fixator 150. When the distal portion 202 of the lead 200 reaches the target site 82, the fixator 150 can be returned to its undeployed compact configuration and be retracted through the lumen 204 of the lead 200, as shown in FIG. 15. The lead 200 can remain installed in the target site 82, as shown in FIG. 2, or advanced more distally in the branching vessel 90 beyond the original target site 82 after the removal of the guidewire 102.

It will be appreciated that, in other aspects, the catheter 250 may be retained during the entire lead delivery procedure, such that the lead is inserted through the catheter 250 and over the guidewire 102, but in such cases slitting of the catheter 250 may not be avoided after lead implantation. In further aspects, the guidewire 102 and the lead 200 can be inserted through the catheter 250 in any order, i.e., guidewire 102 first, or lead 200 first or at the same time. In all aspects, however, the guidewire 102 can first be advanced to the target site 82 of a branching vessel 90 and the fixator 150 be deployed at the target site 82. Only then the distal portion 202 of the lead 200 is advanced to the target site 82 by pushing the lead 200 over the guidewire 102 toward the target site 82, while the guidewire 102 remains fixed. Specifically, the lead 200 can be advanced to the target site 82 in a climbing-like or zip line-like manner by pulling and tensioning the guidewire 102 while the guidewire 102 remains anchored with the deployed fixator 150 at the target site 82.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A medical method comprising:
providing an electrically conductive lead of a medical device comprising a distal tip portion and a lumen defined thereby terminating at a distal opening defined at the distal tip portion;
inserting a distal end of a cannulated catheter through cardiac tissue into a main cardiac vessel, wherein the distal end of the cannulated catheter terminates in a tip opening;
inserting a lead delivery device through the catheter and out the tip opening of the distal end thereof into the main cardiac vessel, the lead delivery device including a guidewire and a fixator coupled to the guidewire in proximity to a distal tip of the guidewire, wherein the fixator is configurable in a deployed expanded shape having a width greater than the tip opening of the distal end of the catheter and an undeployed compact shape having a width less than the tip opening of the distal end of the catheter and less than the distal opening defined at the distal tip portion of the electrically conductive lead;
advancing the inserted lead delivery device to a target site in a branching vessel with the fixator configured in the undeployed compact shape;
deploying the fixator, after the fixator in the undeployed compact shape has been advanced beyond the tip opening of the cannulated catheter, to the deployed expanded shape having multiple contact surfaces such that the multiple contact surfaces can press against an internal lumen of the branching vessel with a holding fixation force to temporarily anchor the guidewire of the advanced lead delivery device in the branching vessel, the holding fixation force being of an amount that allows the guidewire to be pulled in tension without being dislodged from the internal lumen of the branching vessel while the electrically conductive lead of the medical device is pushed over the guidewire, the contact surfaces of the deployed expanded shape being longitudinally offset from one another and on opposite sides of a longitudinal axis of the guidewire;
removing the catheter, as well as any and all other catheters, from around the anchored guidewire, prior to pulling and tensioning the anchored guidewire while pushing the electrically conductive lead of the medical device over the guidewire and to the target site;
pulling and tensioning the anchored guidewire while pushing the electrically conductive lead of the medical device over the guidewire and to the target site, after removing any and all catheters;
returning the fixator to the undeployed compact shape, after pushing the lead to the target site; and
retracting the fixator through the distal opening defined at the distal tip portion and through the lumen of the electrically conductive lead and alongside an internal conductive coil of the electrically conductive lead within the lumen, after returning the fixator to the undeployed compact shape, wherein the fixator is returned to the undeployed compact shape before the fixator in the undeployed compact shape is retracted through the distal opening defined at the distal tip portion of the electrically conductive lead.

2. The method of claim 1, wherein the holding fixation force is equal to or greater than about 2.24 N.

3. The method of claim 2, wherein pushing the lead over the guidewire comprises advancing the lead in a climbing manner.

4. The method of claim 1, wherein the deployed expanded shape of the fixator has a width of approximately 5 mm.

5. The method of claim 1, wherein returning the fixator to the undeployed compact shape comprises contracting the fixator to a compact width equal to or less than approximately 0.483 mm.

6. The method of claim 1, further comprising:
advancing the inserted lead delivery device to another site in the branching vessel outside of the lumen of the lead;
deploying the fixator to the deployed expanded shape having multiple contact surfaces to temporarily anchor the guidewire of the advanced delivery device to the another site in the branching vessel;
pulling and tensioning the anchored guidewire while pushing the electrically conductive lead of the medical device over the guidewire and to the another site in the branching vessel;
returning the fixator to an undeployed compact shape after pushing the electrically conductive lead to the another site in the branching vessel; and
retracting the fixator through the lumen of the electrically conductive lead and alongside an internal conductive coil of the electrically conductive lead within the lumen after pushing the electrically conductive lead to the another site in the branching vessel and returning the fixator to the undeployed compact shape.

7. The method of claim 1, further comprising advancing the electrically conductive lead of the medical device more distally in the branching vessel beyond the target site after removal of the guidewire.

8. The method of claim 1, wherein the multiple contact surfaces of the expanded shape of the fixator have a symmetrical profile.

9. The method of claim 1, wherein the multiple contact surfaces of the expanded shape of the fixator have a non-symmetrical profile.

* * * * *